(12) United States Patent
Sheridan et al.

(10) Patent No.: US 11,007,325 B2
(45) Date of Patent: May 18, 2021

(54) DOSAGE TRACKING APPARATUS, DOSAGE TRACKING SYSTEM, AND RELATED METHODS OF USE

(71) Applicant: Verily Life Sciences LLC, South San Francisco, CA (US)

(72) Inventors: Martin Sheridan, Redwood City, CA (US); Benjamin Krasnow, Redwood City, CA (US)

(73) Assignee: Veriliy Life Sciences LLC, South San Francisco, CA (US)

( * ) Notice: Subject to any disclaimer, the term of this patent is extended or adjusted under 35 U.S.C. 154(b) by 150 days.

(21) Appl. No.: 16/298,597

(22) Filed: Mar. 11, 2019

(65) Prior Publication Data
US 2019/0321559 A1 Oct. 24, 2019

Related U.S. Application Data

(60) Provisional application No. 62/743,102, filed on Oct. 9, 2018, provisional application No. 62/661,963, filed on Apr. 24, 2018.

(51) Int. Cl.
| | |
|---|---|
| *A61M 5/315* | (2006.01) |
| *A61M 5/24* | (2006.01) |
| *G16H 20/13* | (2018.01) |

(52) U.S. Cl.
CPC ...... *A61M 5/31568* (2013.01); *A61M 5/2422* (2013.01); *A61M 5/31511* (2013.01);
(Continued)

(58) Field of Classification Search
CPC .......... A61M 5/31511; A61M 5/31528; A61M 5/31568; G01F 11/027; G01F 13/00
See application file for complete search history.

(56) References Cited

U.S. PATENT DOCUMENTS

| | | | |
|---|---|---|---|
| 6,277,099 B1 * | 8/2001 | Strowe | A61M 5/31553 604/186 |
| 7,736,343 B2 | 6/2010 | Marshall et al. | |

(Continued)

FOREIGN PATENT DOCUMENTS

| | | |
|---|---|---|
| WO | 2012/046199 A1 | 4/2012 |
| WO | 2018/078178 A1 | 5/2018 |

OTHER PUBLICATIONS

International Search Report and Written Opinion dated Jul. 11, 2019, issued in corresponding International Application No. PCT/US2019/026118, filed Apr. 5, 2019, 14 pages.

*Primary Examiner* — Deanna K Hall
(74) *Attorney, Agent, or Firm* — Christensen O'Connor Johnson Kindness PLLC

(57) ABSTRACT

An apparatus for tracking an amount of dispensed fluid, a system for fluid injection including the apparatus, and related methods of use are described. In an embodiment, the apparatus includes a dosage meter shaped to couple with a leadscrew and a cartridge containing a fluid for injection, and configured to track fluid injection. In an embodiment, the dosage meter includes an index wheel including a plurality of teeth, wherein the index wheel is shaped to position coaxially with a major axis of the leadscrew and to receive rotational motion from the leadscrew; and a cantilevered protrusion positioned to deflect due to contact with the plurality of teeth as the index wheel rotates coaxially with the leadscrew inducing a strain in the cantilevered protrusion, wherein the dosage meter outputs a signal indicative of the strain.

20 Claims, 9 Drawing Sheets

(52) U.S. Cl.
CPC ........ *A61M 5/31528* (2013.01); *G16H 20/13* (2018.01); *A61M 2005/2414* (2013.01); *A61M 2205/52* (2013.01)

(56) References Cited

U.S. PATENT DOCUMENTS

| | | |
|---|---|---|
| 8,961,473 B2 | 2/2015 | Heald |
| 2016/0038676 A1 | 2/2016 | Morris |
| 2016/0067419 A1 | 3/2016 | Morris |
| 2016/0263327 A1 | 9/2016 | Radmer et al. |

* cited by examiner

DOSAGE TRACKING APPARATUS, DOSAGE TRACKING SYSTEM, AND RELATED METHODS OF USE

CROSS-REFERENCES TO RELATED APPLICATIONS

This application claims the benefit of U.S. Provisional Application No. 62/661,963, filed Apr. 24, 2018, and U.S. Provisional Application No. 62/743,102, filed Oct. 9, 2018, the contents of which are hereby incorporated by reference in their entireties.

TECHNICAL FIELD

This disclosure relates to an apparatus for tracking fluid injection, and in particular but not exclusively, relates to an apparatus for tracking an amount of dispensed fluid.

BACKGROUND INFORMATION

A fluid injection system is a device, such as a drug injection pen, for injecting into a subject a quantity of fluid, such as a medication. In the treatment of many diseases, such as diabetes mellitus, it is useful to track quantities of medications injected and corresponding times of injection. However, many conventional drug injection pens are not capable of automatically and accurately tracking injection events, quantities of medications injected, or dates and times of injection events.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of a system, apparatus, and method for dosage tracking of fluid injection are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Measuring a quantity of administered drug and recording the timing of a drug's administration are integral parts of many disease treatments. For many treatments, to achieve a desired therapeutic effect, specific quantities of a drug may be injected at specific times of day. For example, individuals suffering from diabetes mellitus may inject themselves with insulin regularly throughout the day in response to measurements of their blood glucose. The frequency and volume of insulin injections should be carefully tracked and controlled to keep the patient's blood glucose level within a healthy range.

Currently, there are a limited number of methods and/or devices capable of tracking drug administration that do not require a user to manually measure and record the volume, date, and time of injection. For example, a variety of glucose injection syringes/pens have been developed, but there is significant room for advancement in tracking injection volume, date, and time. Thus, the current technology may not be an ideal long-term solution. Embodiments of the apparatuses and systems described herein are well suited for accurately tracking dispensed dosages of a drug.

Figure 1A:
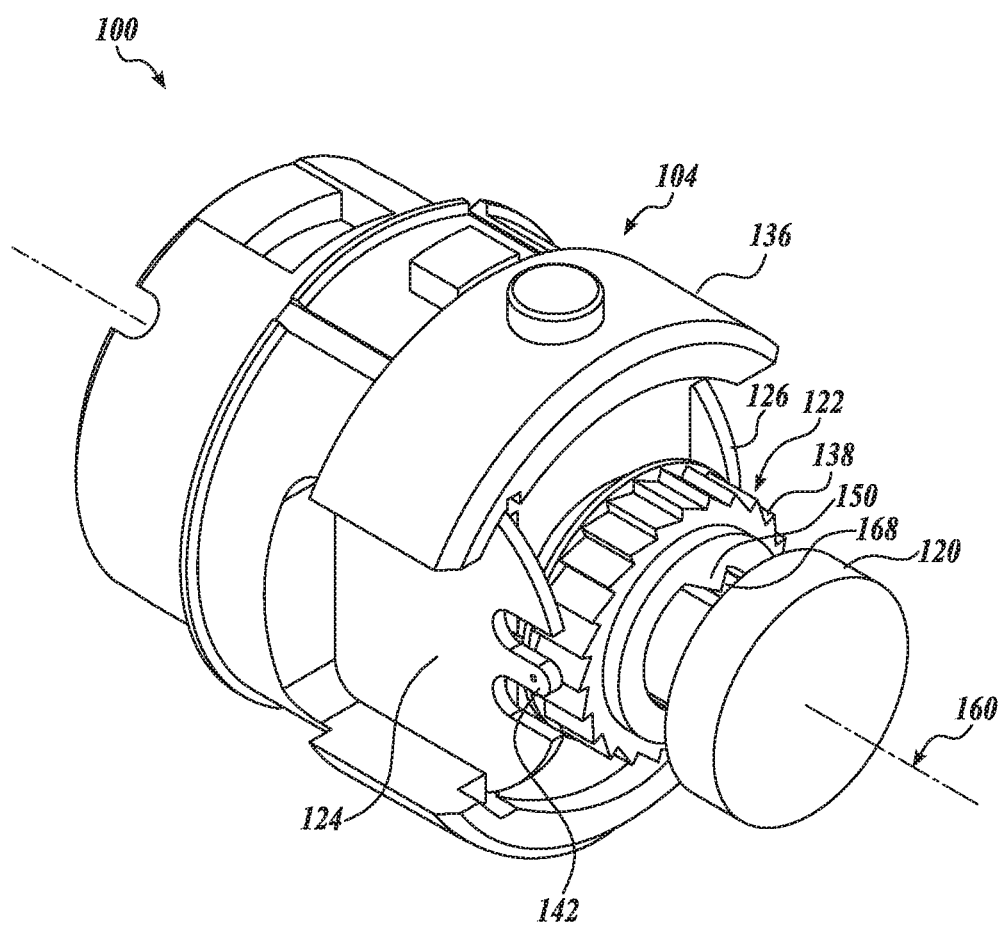
FIG. 1A illustrates a perspective view of an apparatus, in accordance with an embodiment of the disclosure.
Figure 1B:
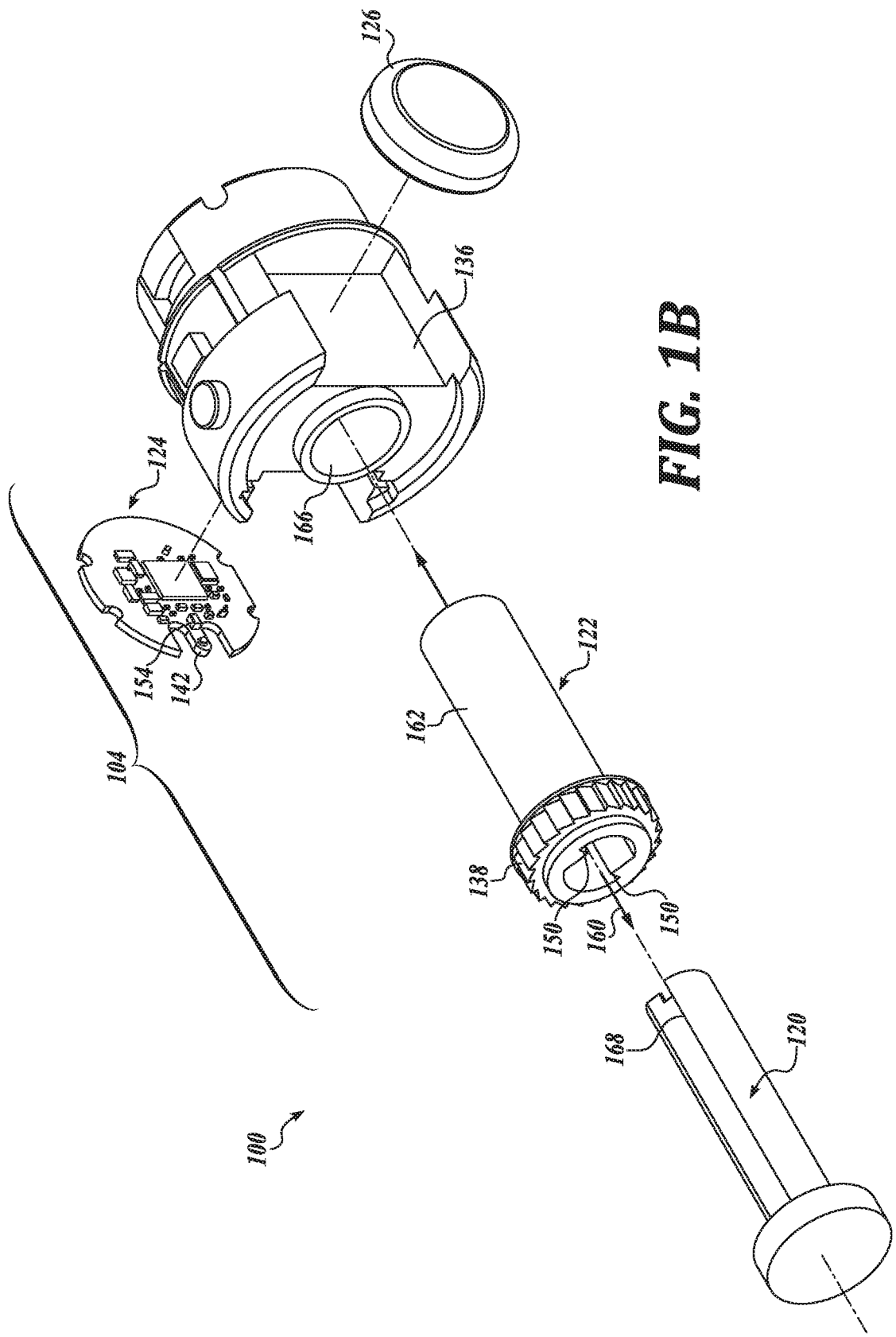
FIG. 1B illustrates an exploded isometric view of the apparatus of FIG. 1A, in accordance with an embodiment of the disclosure.

FIG. 1A illustrates a perspective view of an apparatus 100, in accordance with an embodiment of the disclosure. FIG. 1B illustrates an exploded isometric view of the apparatus 100 of FIG. 1A, in accordance with an embodiment of the disclosure. The apparatus 100 is shown to include dosage meter 104 and leadscrew extender 120. Dosage meter 104 includes an index wheel 122 including a plurality of teeth 138 extending radially from a major axis 160 of index wheel 122, a cantilevered protrusion 142 positioned to deflect due to contact with the plurality of teeth 138, and a bracket 136 shaped and positioned to place the cantilevered protrusion 142 in contact with one of the plurality of teeth 138. In the illustrated embodiment, the cantilevered protrusion 142 is disposed on a circuit board 124 and dosage meter 104 includes a power source 126, shown here as a coin cell battery, coupled to the circuit board 124 and providing power thereto.

As above, cantilevered protrusion 142 is shaped and positioned to deflect radially from a major axis 160 of index wheel 122 as index wheel 122 rotates and a number of the plurality of teeth 138 make contact with the cantilevered protrusion 142. See also FIGS. 2C and 2D. In this regard, a strain is induced in cantilevered protrusion 142 as index wheel 122 rotates. As discussed further herein with respect to FIGS. 2A-2G, dosage meter 104 outputs a signal indicative of the strain, such as from a strain sensor 154 positioned on circuit board 124 disposed adjacent to or on cantilevered protrusion 142. As discussed further herein with respect to FIGS. 2A-2G and FIG. 4, apparatus 100 is configured to track amounts of a dispensed fluid such as by tracking the signals output from the dosage meter 104.

As shown, bracket 136 is shaped to receive circuit board 124 and power source 126 such that as index wheel 122 rotates bracket 136 and cantilevered protrusion 142 remain static relative to such rotational motion. However, it will be understood that components including, for example, bracket 136 and cantilevered protrusion 142 can rotate relative to index wheel 122 and other components in accordance with other embodiments of the disclosure. In the illustrated embodiment, bracket 136 further includes a columnar portion 166 shaped to coaxially and rotatably receive a corresponding columnar portion 162 of index wheel 122. Index wheel 122 rotates as fluid is dispensed from the apparatus 100 due to rotation of the leadscrew (not shown, see for example FIG. 2E). As discussed further herein with respect to FIGS. 2A-2G, cantilevered protrusion 142 deflects due to contact with the plurality of teeth 138.

In certain embodiments, apparatus 100 is suitable to couple with an existing fluid injection system, such as an insulin injection pen. In an embodiment, apparatus 100 including dosage meter 104 and leadscrew extender 120 is shaped to couple with a fluid injector (not shown, see FIG. 2E) and a housing (not shown, see also FIG. 2E) from an existing fluid injection system, such as an existing insulin injection pen, that, for example, does not include a dosage meter. In this regard, apparatus 100 is shaped to be integrated into a fluid injection system as an after-market dosage-tracking apparatus to track, for example, injection events, injection volumes, injection times, and the like. Accordingly, in an embodiment, apparatus 100 is shaped to couple with and count injection events from an existing fluid injection system. By coupling apparatus 100 with an existing fluid injection system, a user may automatically track injection events, injection times, and calculate quantities of fluid injected with the modified fluid injection system including apparatus 100 coupled thereto without manually tracking any such injection metrics.

Figure 2A:
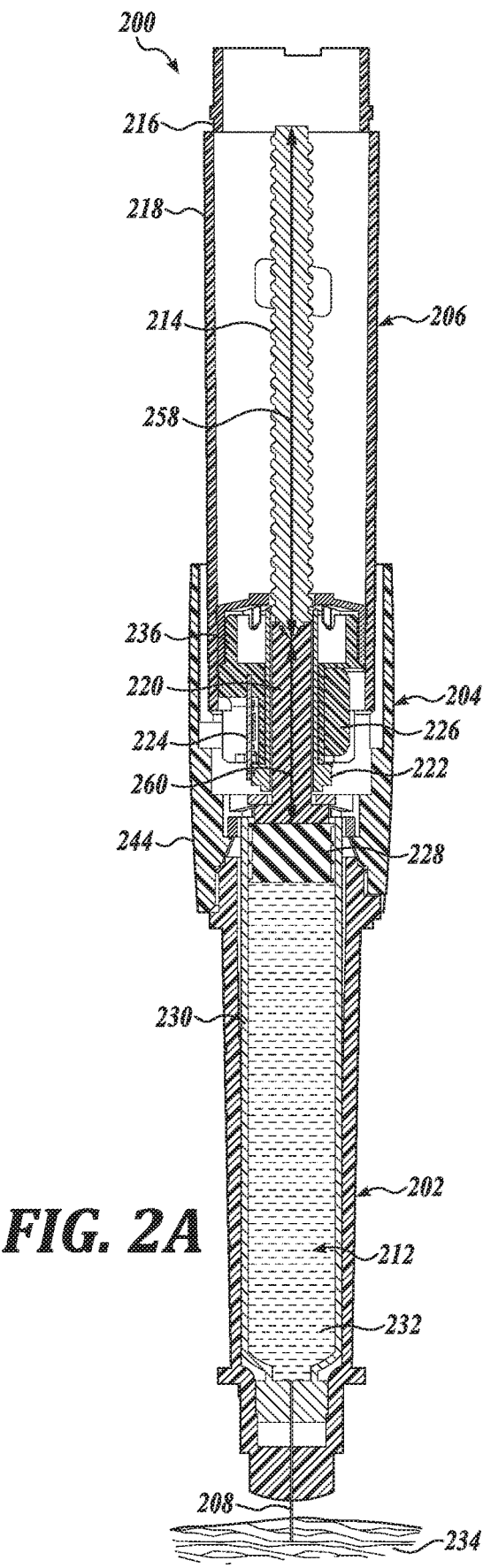
FIGS. 2A and 2B illustrate cross-sectional views of an apparatus, in accordance with an embodiment of the disclosure.
Figure 2B:
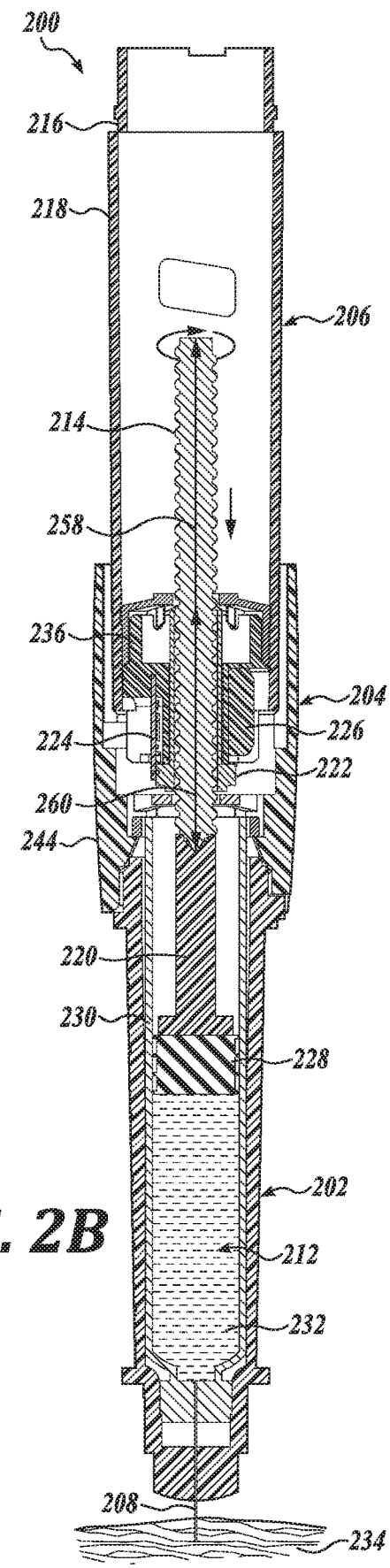

In an embodiment, dosage meter 104 is shaped to couple with a leadscrew and a cartridge containing a fluid for injection (not shown, see FIGS. 2A and 2B). In this regard, index wheel 122 is shaped to position coaxially with a major axis of a leadscrew, such as a leadscrew of the fluid injection system, and to receive rotational motion from the leadscrew. As shown, index wheel 122 includes tabs 150 shaped to extend into and couple with leadscrew extender grooves 168. As discussed further herein, tabs 150 are further shaped to extend into and couple with grooves on a leadscrew (not shown, see FIG. 2E). In this regard, as the leadscrew rotates about a leadscrew major axis the rotational motion of the leadscrew is received by the index wheel 122 and the index wheel 122 rotates about its own major axis 160. Additionally, as discussed further herein with respect to FIGS. 2C and 2D, leadscrew extender 120 is shaped to transfer the rotational motion of the leadscrew to the index wheel 122. As above, cantilevered protrusion 142 does not receive the rotational motion of the leadscrew and remains static with respect to the rotational motion.

As above, in an embodiment, the apparatus 100 further includes leadscrew extender 120. Leadscrew extender 120 is shaped as an extension of a leadscrew to accommodate for additional length of dosage meter 104 and to receive rotational and translational motion of the leadscrew. In this regard, leadscrew extender 120 is shaped to receive motion of the leadscrew along the major axis of the leadscrew. Accordingly, an existing fluid injection system modified to include apparatus 100 including dosage meter 104 and leadscrew extender 120 both dispenses fluid from the fluid injection system and tracks injection events. Further, the leadscrew extender 120 ensures that more or all of the fluid in a cartridge of the fluid injection system is dispensed with apparatus installed. Without the leadscrew extender 120, a fluid injection system modified to include apparatus 100 may not dispense all of the fluid if, for example, the leadscrew is not long enough by itself to displace a plunger head to a far end of a cartridge.

FIGS. 2A and 2B illustrate cross-sectional views of an apparatus 200, in accordance with an embodiment of the disclosure. In an embodiment, the apparatus 200 is the apparatus 100 of FIG. 1. Apparatus 200 includes housing 202, dosage meter 204, and fluid injector 206. Housing 202 includes needle 208, shown here disposed in a portion of skin 234, and cavity 212 shaped to accept cartridge 230. Cartridge 230 includes plunger head 228 and contains fluid 232. Needle 208 is shown coupled to cartridge 230 and in fluidic communication with fluid 232, such as a medication. In this regard, and as discussed further herein, as fluid injector 206 translates linearly and depresses plunger head 228, fluid 232 is dispensed from cartridge 230 through needle 208.

Housing 202 is coupled to fluid injector 206 to dispense fluid 232. Fluid injector 206 includes fluid injector housing 218, leadscrew 214 disposed in fluid injector housing 218 and having major axis 258, and fluid delivery control wheel 216 to select an amount of fluid 232 dispensed.

Dosage meter 204 includes dosage meter housing 244 (see FIGS. 2A and 2B), index wheel 222 disposed within dosage meter 204 housing, bracket 236, cantilevered protrusion 242 shown here as part of circuit board 224, power source 226 operably coupled to circuit board 224, and leadscrew extender 220. In the illustrated embodiment, leadscrew extender 220 is positioned to be in contact at a first end of the leadscrew extender 220 with a portion of the cartridge 230 (here plunger head 228) and at a second end of the leadscrew extender 220 with an end of the leadscrew 214. As discussed further herein, leadscrew extender 220 couples linear motion between the leadscrew 214 and cartridge 230 and rotational motion between the fluid injector 206 and dosage meter 204. In this regard, leadscrew extender 220 translates linear motion of leadscrew 214 to dispense fluid 232, which is received by housing 202 to dispense fluid 232. Additionally, as discussed further herein with respect to FIGS. 2C and 2D, leadscrew extender 220 translates rotational motion of leadscrew 214 to track injection events in conjunction with dosage meter 204.

FIG. 2A illustrates apparatus 200 in a first configuration, for example, prior to rotation and translation of leadscrew 214 about and along its major axis 258. In this regard, plunger head 228 is in a first position near the rear of the cartridge 230. FIG. 2B illustrates leadscrew 214 rotating about major axis 258 and translating linearly along major axis 258, thereby depressing plunger head 228 from the rear of cartridge 230 and dispensing fluid 232 from cartridge 230. As plunger head 228 moves from the rear of the cartridge 230 to the front of the cartridge 230, fluid 232 is dispensed from the cartridge and through needle 208.

Figure 2D:
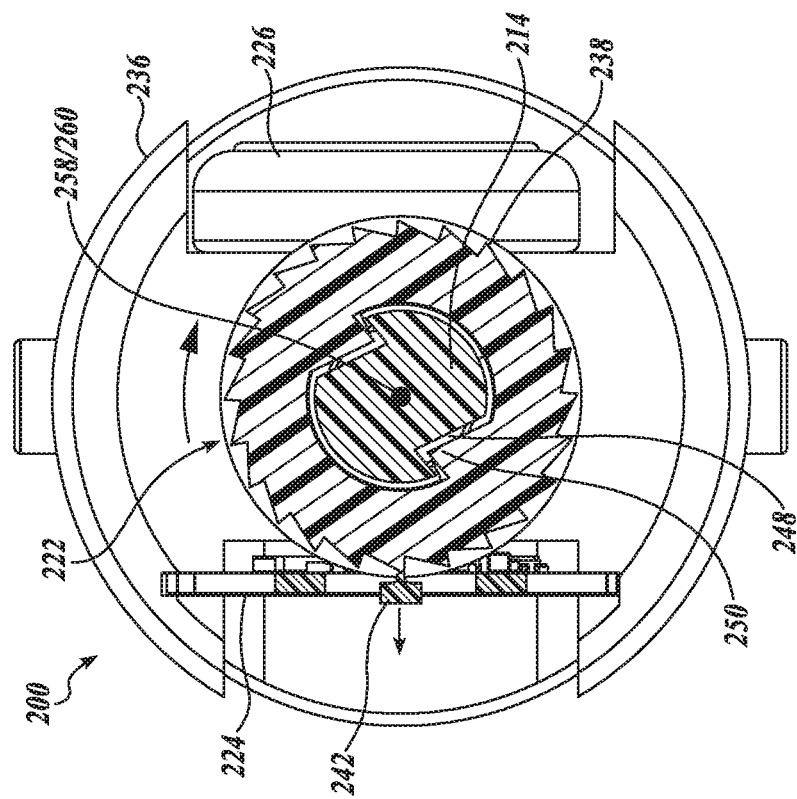
FIGS. 2C and 2D illustrate other cross-sectional views of the apparatus of FIGS. 2A and 2B, in accordance with an embodiment of the disclosure.
Figure 2C:
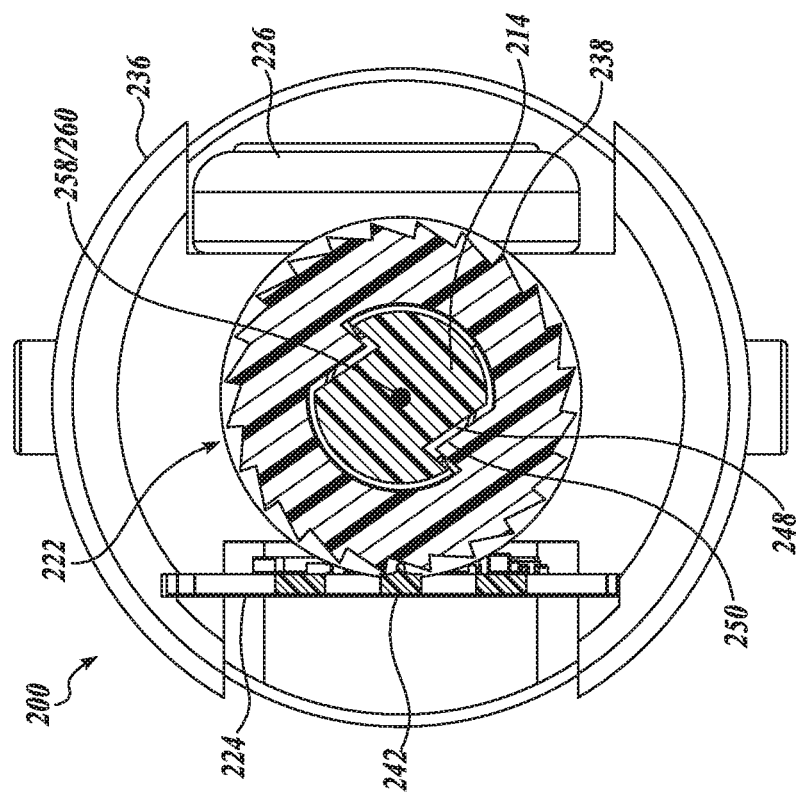

FIGS. 2C and 2D illustrate other cross-sectional views of the apparatus 200 of FIGS. 2A and 2B, in accordance with an embodiment of the disclosure. As above, apparatus 200 includes dosage meter 204 to measure an amount of fluid dispensed by apparatus 200. In the illustrated embodiment, the index wheel 222 has a major axis 260 and is positioned coaxially with major axis 258 of the leadscrew 214. Index wheel 222 is coupled to fluid injector 206, shown here coupled to the leadscrew 214, to rotate coaxially with the leadscrew 214 when the apparatus 200 dispenses the fluid from the cartridge 230. As shown, index wheel 222 includes tabs 250 shaped to extend into and couple with leadscrew grooves 248. In this regard, as leadscrew 214 rotates about leadscrew major axis 258 the rotational motion of the leadscrew 214 is received by the index wheel 222 and the index wheel 222 rotates about its own major axis 260, shown here coaxial with major axis 258. In an embodiment, an interior of a columnar portion 262 of the index wheel 222 including tabs 250 extends into and couples with the leadscrew 214 to receive the rotational motion. (See FIG. 2E).

Figure 2E:
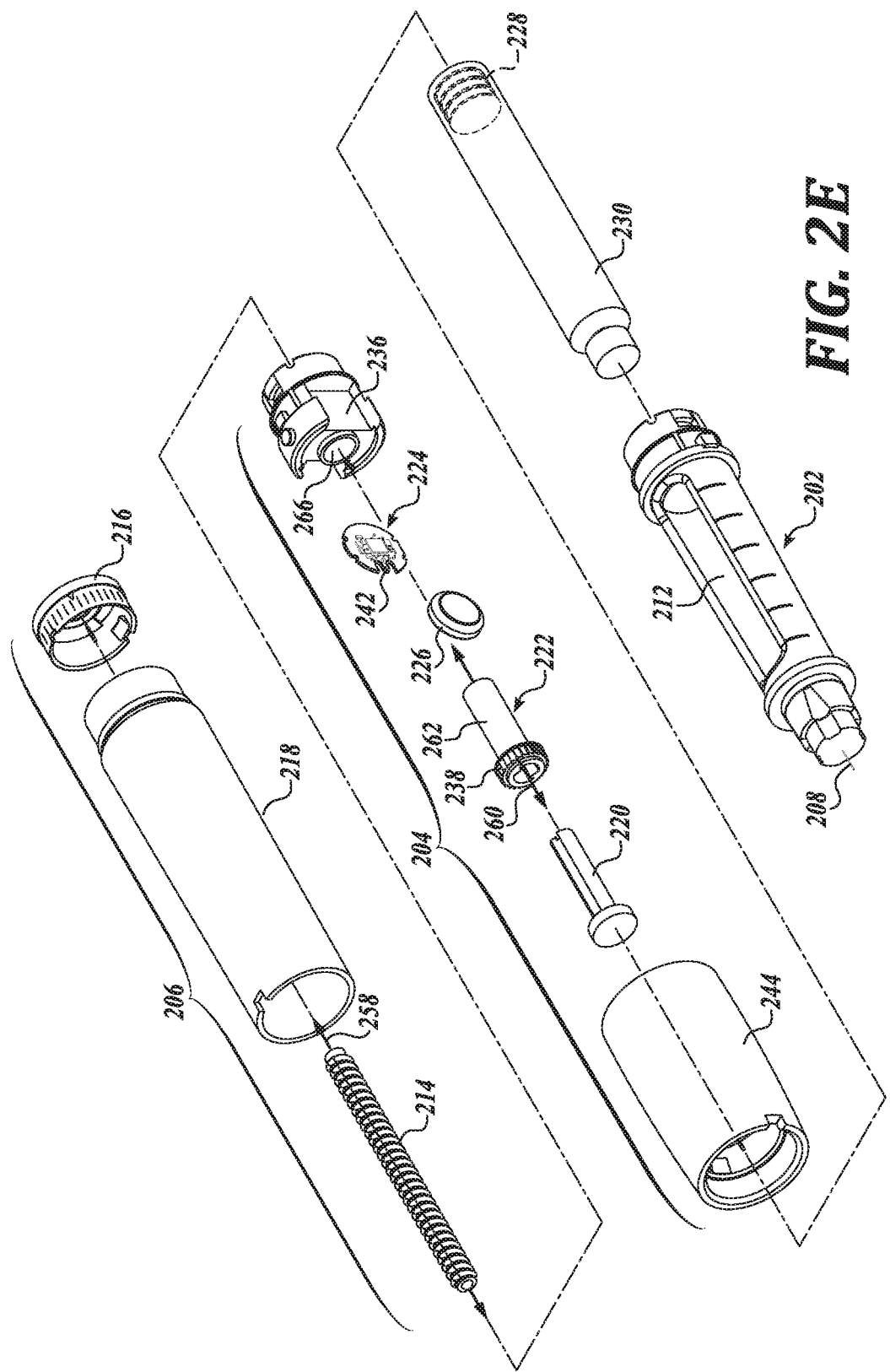
FIG. 2E illustrates an exploded isometric view of the apparatus of FIGS. 2A and 2B, in accordance with an embodiment of the disclosure.
Figure 2F:
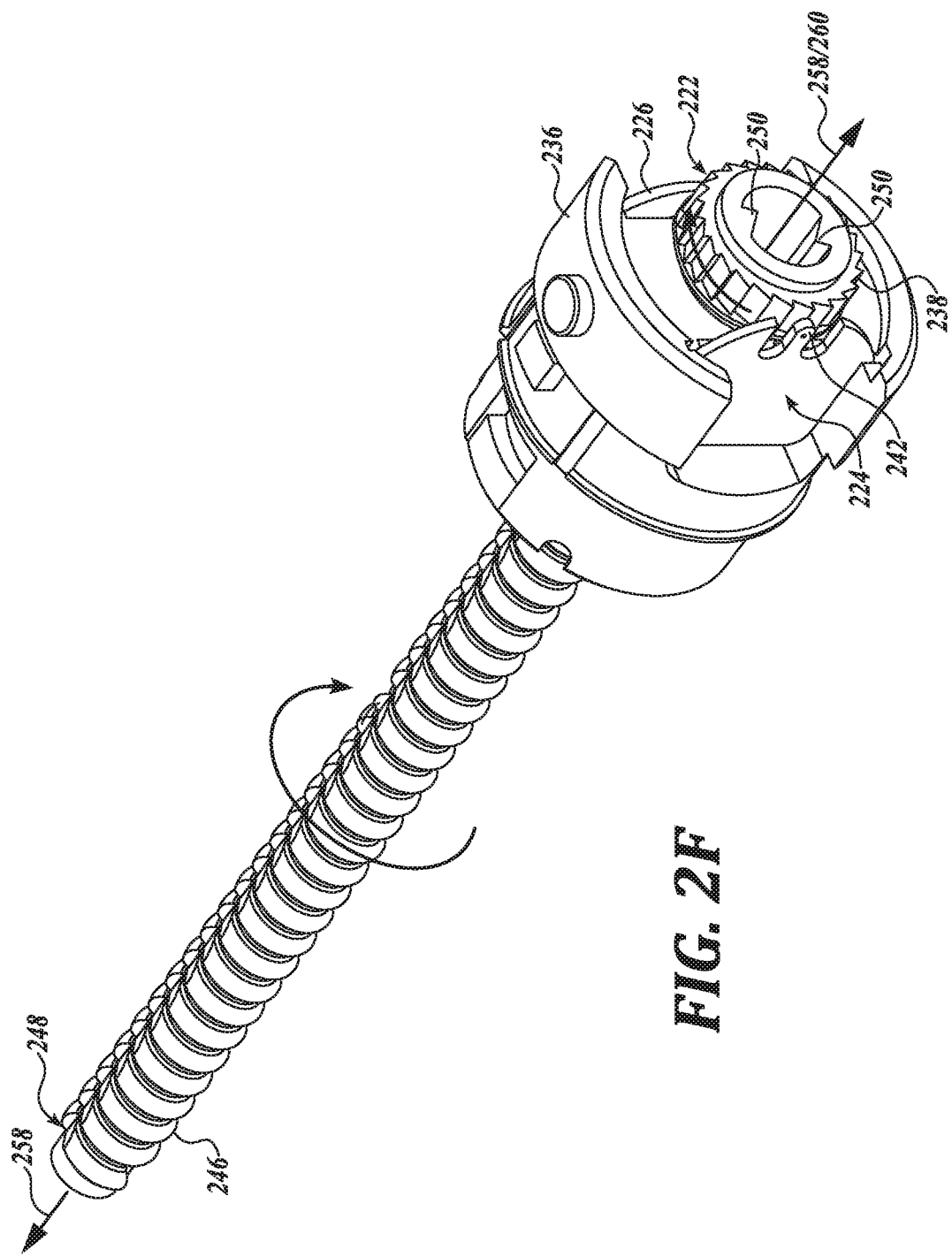
FIG. 2F illustrates a perspective view of a portion of the apparatus of FIGS. 2A and 2B, in accordance with an embodiment of the disclosure.

As shown, index wheel 222 does not, however, couple with leadscrew threads 246 (see FIGS. 2E and 2F). In this regard, index wheel 222 receives the rotational motion of leadscrew 214, but does not receive the linear translation of leadscrew 214. Accordingly, as leadscrew 214 rotates about and translates along major axis 258, index wheel 222 rotates with, but does not translate with, leadscrew 214. In this regard, index wheel 222 is shaped to track injection events without translating along major axis 258.

Index wheel 222 includes a plurality of teeth 238 extending radially from major axis 260 of index wheel 222. Cantilevered protrusion 242 is positioned to deflect due to contact with the plurality of teeth 238 as the index wheel 222 rotates coaxially with the leadscrew 214. Bracket 236 is shaped to place the cantilevered protrusion 242 in contact with the plurality of teeth 238. Additionally, bracket 236 includes a columnar portion 266 (See FIG. 2E) positioned coaxially with the major axis 258 of the leadscrew 214 and positioned to accept a portion of the leadscrew 214. However, unlike the index wheel 222, the bracket 236 does not receive the rotational motion of the leadscrew 214. Accordingly, in this regard, as the index wheel 222 rotates about its major axis 260, the cantilevered protrusion 242 is stationary relative the rotational motion of the index wheel 222. Thus, as the leadscrew 214 rotates, the plurality of teeth 238 pass over the cantilevered protrusion 242 repeatedly deflecting the cantilevered protrusion 242 radially from major axis 260 of index wheel 222. As discussed further herein, such repeated deflection induces repeated strain in the cantilevered protrusion 242, which outputs signals indicative of the strain that can be correlated to an injection event and, in certain embodiments, an injection volume.

In the illustrated embodiment, each of the plurality of teeth 238 has a wave-like cross section including a gradual increase in tooth height relative to major axis 260 followed by a precipitous decrease in tooth height. In this regard, as index wheel 222 rotates about its major axis 260, cantilevered protrusion 242 gradually deflects as it travels over the gradual increase followed by a precipitous return to an initial position as the cantilevered protrusion 242 passes over the precipitous decrease. Such a rapid change in deflection generates an easily measured signal indicative of strain of the cantilevered protrusion 242. However, as one of ordinary skill in the art will appreciate, a cross section of the plurality of teeth 238 can assume other configurations and have other cross sectional shapes, such as triangular, undulating, trapezoidal, and the like, suitable to deflect cantilevered protrusion 242, induce a strain therein, and generate a detectable signal indicative of the strain.

FIG. 2C illustrates dosage meter 204 in a first position in which cantilevered protrusion 242 is in contact with one of the plurality of teeth 238 such that the cantilevered protrusion 242 is not deflected. FIG. 2D illustrates dosage meter 204 in which index wheel 222 is rotated coaxially with leadscrew 214 from the first position to a second position in which cantilevered protrusion 242 is in a contact with a portion of one of the plurality of teeth 238 that extends radially farther from major axis 260 than in the first position. Accordingly, in the illustrated embodiment of FIG. 2D, the cantilevered protrusion 242 deflects radially from the major axis 258 of the index wheel 222. In this regard, cantilevered protrusion 242 is deflected due to contact with the plurality of teeth 238 as the index wheel 222 rotates coaxially with the leadscrew 214 inducing a strain in the cantilevered protrusion 242. As discussed further herein with respect to FIG. 2G, cantilevered protrusion 242 outputs a signal indicative of the strain, which in turn is correlated to an injection event of the apparatus 200.

FIG. 2F illustrates a portion of the apparatus 200 of FIGS. 2A and 2B, in accordance with an embodiment of the disclosure. The illustrated embodiment shows a portion of dosage meter 204, including bracket 236, circuit board 224 including cantilevered protrusion 242, index wheel 222, and power source 226, as well as leadscrew 214. As shown, index wheel 222 and circuit board 224 are positioned by bracket 236 to place the plurality of teeth 238 in contact with cantilevered protrusion 242. Additionally, circuit board 224 and power source 226 are positioned in bracket 236 to operably couple power source 226 to circuit board 224. Major axes 258 and 260 are coaxial and leadscrew 214 is coupled with index wheel 222. In this regard, index wheel 222 is positioned to receive rotational motion from leadscrew 214. Further, as leadscrew 214 rotates cantilevered protrusion 242 is deflected.

As above, dosage meter 204 is shaped to couple to housing 202 at a first end and couple to fluid injector 206 at a second end. See, for example, FIGS. 2A and 2B. In this regard, dosage meter 204 registers rotation of leadscrew 214 during an injection event. This is in contrast to a dosage meter shaped to directly register rotation of, for example, a fluid delivery control wheel, such as fluid delivery control wheel 216. As above, fluid delivery control wheel 216 is shaped to select an amount of fluid dispensed. Often when a user is rotating a fluid delivery control wheel, for example, to select the amount of fluid delivered the user will initially select an amount that is too great by rotating the fluid delivery wheel past a correct volume indication. The user may then rotate the fluid delivery wheel back to a correct volume. Dosage meters directly coupled to fluid delivery control wheels may not have a way to account for a user's over-rotation of the fluid delivery control wheel. In this regard, such a dosage meter may incorrectly register a quantity of dispensed fluid that is greater than the amount of fluid actually injected. In an embodiment, leadscrew 214 only rotates during an injection event and not, for example, when a user selects an injection amount with fluid delivery control wheel 216. In this regard, dosage meter 204 registers injection events and corresponding injection volumes rather than injection volumes initially selected by user that are not ultimately injected.

Figure 2G:
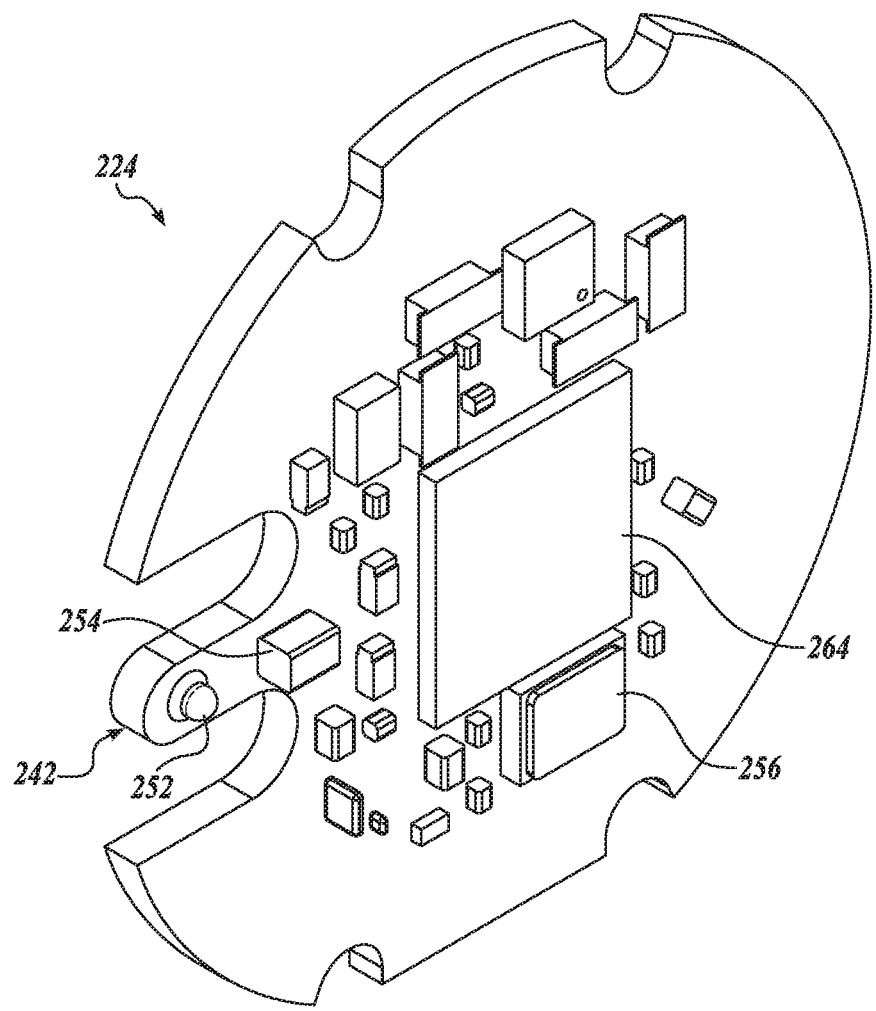
FIG. 2G illustrates a circuit board of the apparatus of FIGS. 2A and 2B, in accordance with an embodiment of the disclosure.

FIG. 2G illustrates a circuit board 224 of the apparatus 200 of FIGS. 2A and 2B, in accordance with an embodiment of the disclosure. Circuit board 224, disposed in dosage meter 204, includes cantilevered protrusion 242, ball 252, strain sensor 254, and controller 256. In the illustrated embodiment, circuit board 224 includes cantilevered protrusion 242 as a cutout of the circuit board 224. Circuit board 224 further includes strain sensor 254, shown here disposed on a portion of the cantilevered protrusion 242. In this regard, the strain sensor 254 is positioned to output a signal indicative of a strain of the cantilevered protrusion 242, such as when the cantilevered protrusion 242 is in contact with and deflected by the plurality of teeth 238, as discussed further herein with respect to FIGS. 2C and 2D.

In an embodiment, the strain sensor 254 is selected from the group consisting of a capacitive strain sensor, a piezoelectric strain sensor, and a resistive strain sensor.

As shown, circuit board 224 further includes ball 252 disposed on a portion of cantilevered protrusion 242. When, for example, bracket 236 positions circuit board 224 in contact with the plurality of teeth 238, ball 252 is positioned to directly contact the plurality of teeth 238. In an embodiment, ball 252 provides a smooth, hard surface on which the plurality of teeth 238 contacts the cantilevered protrusion 242. In the illustrated embodiment, ball 252 is shown as a hemispherical ball; however, it is understood that other shapes and configurations suitable to move over the plurality of teeth 238 are included in the described embodiments, thus providing a reliable, easily detected signal indicative of cantilevered protrusion 242 deflection.

As above, circuit board 224 includes controller 256. In an embodiment, controller 256 is operatively coupled to strain sensor 254. In this regard, controller 256 is configured to register and track signals output by strain sensor 254 indicative of strain on cantilevered protrusion 242. Further, in an embodiment, controller 256 is operatively coupled to dosage meter 204. Such coupling can include direct coupling, such as through a wire, conductive trace, and the like. Likewise, such coupling can be wireless, such as through Bluetooth, RFID, or other wireless communications technologies.

Figure 3:
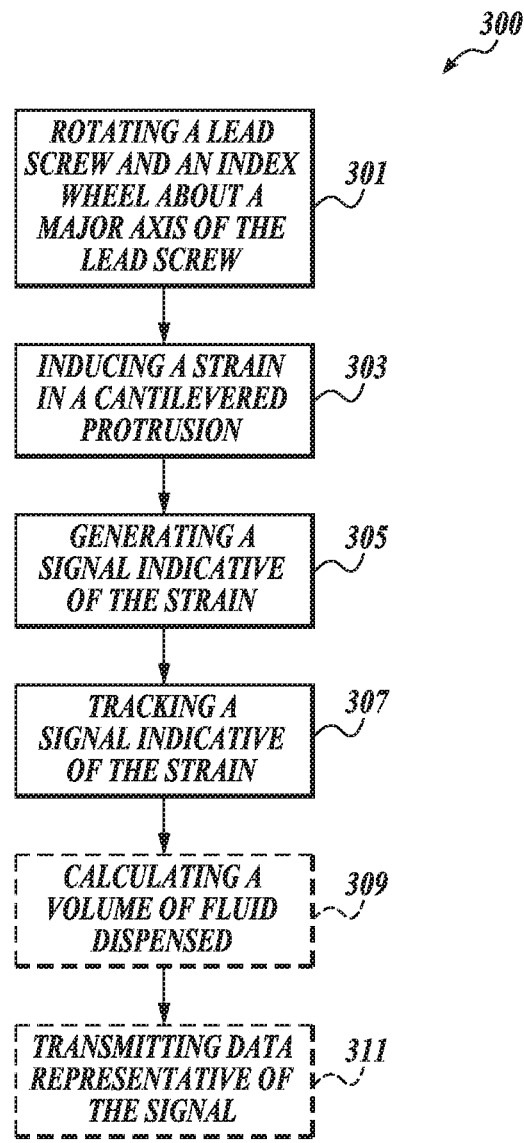
FIG. 3 is a schematic illustration of a method of measuring a quantity of fluid dispensed from an apparatus, in accordance with an embodiment of the disclosure.

As above, controller 256 can include logic. In an embodiment, controller 256 includes logic that when executed by controller 256 causes apparatus 200 to record the electrical signals indicative of the fluid dispensed into a dispensing log. One of ordinary skill in the art will appreciate that the controller 256 including tangible machine-readable storage medium may be static (e.g., have logic in hardware), or dynamic (e.g., have programmable memory that can receive updates). In an embodiment, the logic includes logic that when executed by the controller 256 causes the apparatus 200 to perform operations including: tracking the signal output from the dosage meter 204. As discussed further herein with respect to FIGS. 2C and 2D, such signal output can be indicative of strain on cantilevered protrusion 242 and output from, for example, strain sensor 254. Further, in an embodiment, controller 256 includes logic that when executed by the controller 256 causes the apparatus 200 to perform operations including: registering the signal as an injection event of the fluid 232; and calculating a number of injection events of the fluid 232. In this regard, the logic may be configured to determine a number of instances of strain on cantilevered protrusion 242 to determine a number of injection events, as discussed further herein with respect to method 300 and FIG. 3.

As shown in, for example, FIGS. 2C and 2D, the plurality of teeth 238 are approximately evenly spaced and are approximately equidistant from major axis 260. In this regard, as leadscrew 214 rotates about major axis 258 and translates along major axis 258, each signal output indicative of strain on cantilevered protrusion 242 corresponds to an at least approximately equal volume of fluid dispensed. In this regard, each signal indicative of an injection event can be correlated with an injection volume. Accordingly, in an embodiment, controller 256 further includes logic that when executed by the controller 256 causes the apparatus 200 to perform operations including: calculating a quantity of the fluid 232 dispensed based, at least in part, on the number of injection events.

Circuit board 224 including controller 256 is operably coupled to a power source 226, such as a battery. As shown in, for example, FIGS. 2C and 2D, bracket 236 is shaped to accept both circuit board 224 and power source 226. Additionally, bracket 236 is shaped to operably couple circuit board 224 and power source 226. Circuit board 224 further includes a transceiver 264 (See FIG. 2G) coupled to the controller 256 to send and receive data, such as data including a number of injection events and/or a quantity of fluid 232 dispensed. In an embodiment, controller 256 further includes logic that when executed by the controller 256 causes the apparatus 200 to perform operations including: instructing the transceiver 264 to send the data to an external device (not shown, see FIG. 4), such as a smartphone, tablet, general purpose computer, distributed system, servers connected to the internet, or the like, wherein the data includes information indicative of the number of injection events.

Figure 4:
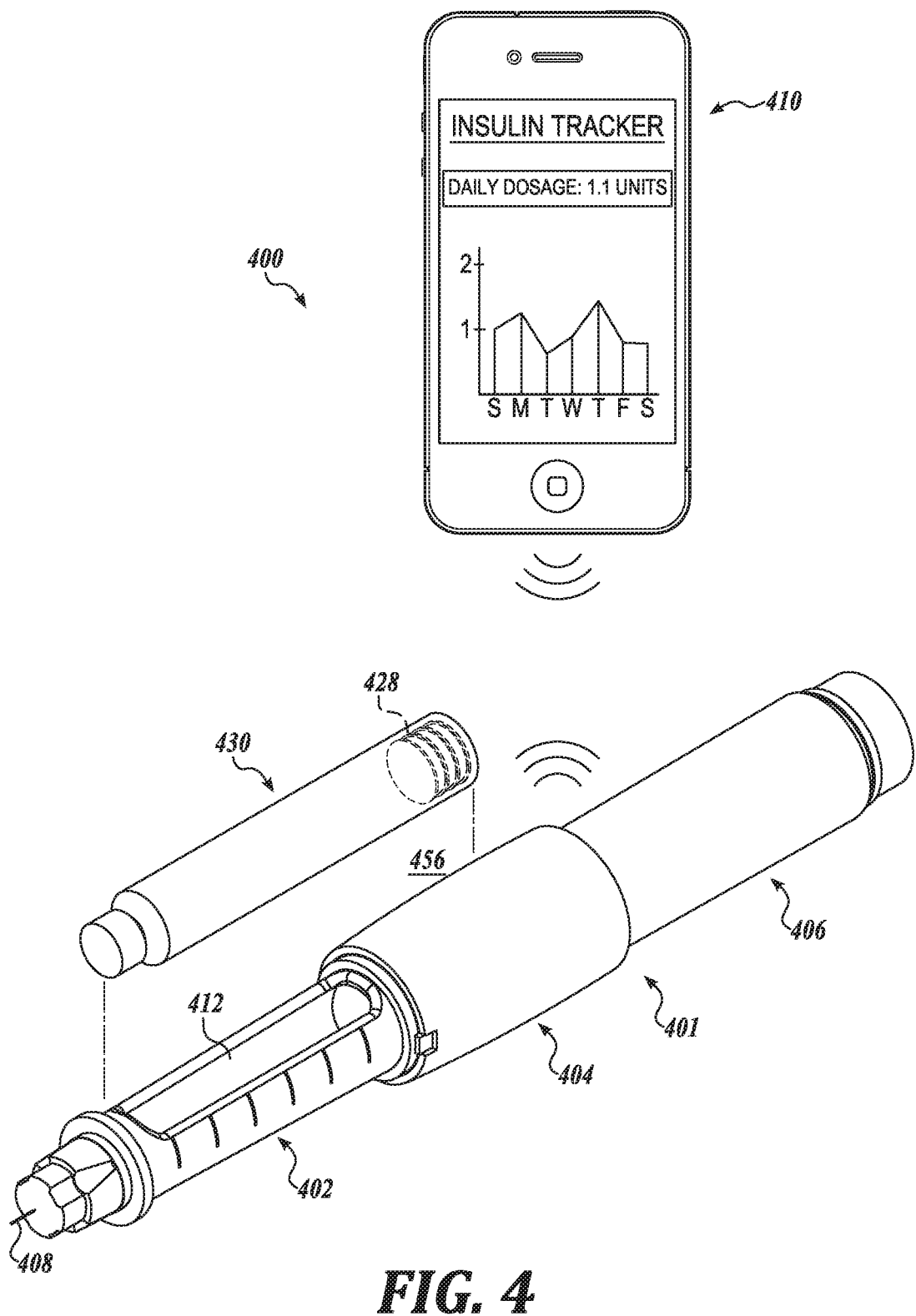
FIG. 4 illustrates a system, in accordance with an embodiment of the disclosure.

FIG. 4 illustrates system 400, shown here as a fluid injection system 400, in accordance with an embodiment of the disclosure. Fluid injection system 400 includes an apparatus 401 and processing device 410 (e.g., a portable computing device, a smart phone, etc.). Apparatus 401 includes housing 402, a dosage meter 404, and a fluid injector 406. In an embodiment, apparatus 401 is an example of apparatuses 100 and/or 200.

Housing 402 is shaped to accept a cartridge 430 containing a fluid, such as a medication. In the illustrated embodiment, housing 402 includes cavity 412 shaped to accept cartridge 430 and needle 408 positioned to be in fluidic contact with fluid disposed in cartridge 430 when cartridge 430 is disposed in housing 402. In one embodiment, cartridge 430 may be disposed in an insert which screws/snaps onto or into the bulk of housing 402. However, as one of ordinary skill in the art will appreciate, apparatus 401 can assume other configurations and have other components.

Cartridge 430 includes plunger head 428. In the depicted embodiment, plunger head 428 starts near a rear portion of cartridge 430 and is pushed forward in cartridge 430 by the fluid injector 406. (See also FIGS. 2A and 2B). This forces medication/fluid out of the narrow end of cartridge 430 and through needle 408 when a fluid is dispensed.

A dosage meter 404 is also disposed in the apparatus 401 to track the rotational motion of the fluid injector 406. In the illustrated embodiment, dosage meter 404 is shown coupled on a first side to fluid injector 406 and on a second side to housing 402. As described further herein with respect to FIGS. 2A-2G, the dosage meter 404 encodes the rotational motion of the fluid injector 406 to track the amount of fluid dispensed and further outputs a signal indicative of the rotation or fluid dispensed.

As shown, controller 456 including circuitry is also disposed in apparatus 401, as part of the dosage meter 404. It is appreciated that this circuitry, which described further herein with respect to FIG. 2G, may be disposed anywhere in apparatus 401 (e.g., in housing 402 or fluid injector 406), and in some instances, logic may be distributed across multiple devices.

Processing device 410 (e.g., a smartphone, tablet, general purpose computer, distributed system, servers connected to the internet, or the like) may be coupled to receive signal output from apparatus 401 to store/analyze this data. For instance, in the depicted embodiment, processing device 410 is a smartphone, and the smartphone has an application running recording how much insulin has been dispensed from apparatus 401. In the illustrated embodiment, the application plots how much insulin has been injected by the user over a historical period of time (e.g., day, week, month, or the like). In this embodiment, a power source (not shown, see for example FIG. 2A) is electrically coupled to the controller 456 in apparatus 401, and a transceiver (not shown, see for example FIG. 2G) is electrically coupled to the controller 456 to send and receive data to/from processing device 410. Here, data includes information indicative of a quantity of the fluid dispensed. The transceiver may include Bluetooth, RFID, or other wireless communications technologies.

A method of measuring a quantity of fluid dispensed from an apparatus, such as, for example, apparatuses 100 and 200 or a system 400 comprising apparatus 401, will now be described. In this regard, attention is directed to FIG. 3, which is a schematic illustration of a method 300 of measuring a quantity of fluid dispensed from an apparatus, in accordance with an embodiment of the disclosure. One of ordinary skill in the art having the benefit of the present disclosure will appreciate that the blocks of method 300 may occur in any order and even in parallel. Additionally, blocks may be added to, or removed from, method 300 in accordance with the teachings of the present disclosure.

The method may begin with block 301, which includes rotating a leadscrew of the apparatus along with an index wheel of the apparatus about a major axis of the leadscrew. In this regard, a fluid is dispensed from the apparatus, as discussed further herein with respect to FIGS. 2A and 2B. In some embodiments method 300 may further include a user actuating a fluid injection button disposed on a proximal end of the apparatus, opposite a dispensing end to initiate rotating the leadscrew and index wheel. In such an embodiment, the leadscrew is rotated and fluid is dispensed from the apparatus in response to the user actuating the button.

Block 301 may be followed by block 303, which may include inducing a strain in a cantilevered protrusion disposed to engage the index wheel as the index wheel rotates. It will be appreciated that, in the depicted embodiment, inducing the strain occurs at the same time as rotating the leadscrew and the index wheel. As discussed further herein with respect to FIGS. 2C and 2D, in an embodiment, the index wheel includes a plurality of teeth positioned to contact the cantilevered protrusion. As the index wheel rotates, one or more of the plurality of teeth deflect the cantilevered protrusion radially from a major axis of the index wheel thereby inducing the strain. In an embodiment, the major axis of the index wheel is coaxial with the major axis of the leadscrew about which each rotates, as discussed further herein with respect to FIGS. 2C and 2D.

Block 303 may be followed by block 305, which may include generating a signal indicative of the strain in a cantilevered protrusion. In an embodiment, generating the signal includes deflecting the cantilevered protrusion with a tooth extending radially from a major axis of the index wheel, wherein the cantilevered protrusion deflects radially from the major axis of the index wheel in response to the tooth pressing against the cantilevered protrusion; and generating with a strain sensor disposed on the cantilevered protrusion and coupled to a controller the signal. As discussed further herein with respect to FIG. 2G, in an embodiment, the strain sensor is disposed on the cantilevered protrusion. In some embodiments, the signal output from the strain sensor may be amplified with amplifiers coupled between the strain sensors and the controller.

Block 305 may be followed by block 307, which may include tracking the signal indicative of the strain. In an embodiment, tracking the signal indicative of the strain includes storing the signal in memory disposed in the apparatus using a controller coupled to receive the signal.

Block 307 may be followed by block 309, which may include calculating a quantity of the fluid dispensed. In an embodiment, calculating a quantity of the fluid dispensed is based, at least in part, on the signal recorded. As discussed further herein with respect to FIGS. 2C and 2D, by registering the signal as an injection event of the fluid, calculating a number of injection events, and correlating an injection event to a volume of fluid injected, the quantity of fluid can be calculated based, in part, on the signal recorded. In an embodiment, block 309 is optional.

Blocks 307 and/or 309 may be followed by block 311, which may include transmitting data representative of the signal to a processing device that is distinct from the apparatus, wherein the processing device calculates the quantity of fluid dispensed. As discussed further herein with respect to FIG. 4, the data representative of the signal may be transmitted to a device distinct from the apparatus such as a smartphone, tablet, general purpose computer, distributed system, servers connected to the internet, or the like. In this regard, a user can, for example, track quantities of dispensed fluid and associated injection times over a period of time, such as a day, week, month, etc. By displaying or otherwise representing aggregated quantities of dispensed fluid with or according to corresponding fluid injection times a user may be able to more easily track quantities, times, and/or dates of dispensed fluid. In an embodiment, block 311 is optional.

In an embodiment, Block 307 is followed by block 311. In this regard, the signal representative of the strain may be transmitted to a device distinct from the apparatus and, for example, calculating a quantity of the fluid dispensed based, at least in part, on the signal recorded may be performed on the device distinct from the apparatus, rather than on the apparatus itself.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An apparatus for measuring an amount of a dispensed fluid, the apparatus comprising:
a dosage meter shaped to couple with a leadscrew and a cartridge containing a fluid for injection, the dosage meter comprising:
an index wheel including a plurality of teeth, wherein the index wheel is shaped to position coaxially with a major axis of the leadscrew and to receive rotational motion from the leadscrew; and
a cantilevered protrusion positioned to deflect due to contact with the plurality of teeth as the index wheel rotates coaxially with the leadscrew inducing a strain in the cantilevered protrusion, wherein the dosage meter outputs a signal indicative of the strain;
a leadscrew extender positioned to be in contact at a first end of the leadscrew extender with a portion of the cartridge and at a second end of the leadscrew extender with an end of the leadscrew; and
a fluid injector comprising:
a fluid delivery control wheel configured to select an amount of fluid dispensed; and
the leadscrew that produces rotational motion about the leadscrew major axis when the apparatus dispenses the fluid from the cartridge, wherein the leadscrew is configured to rotate during an injection event and not in selecting the amount of fluid dispensed with the fluid delivery control wheel.

2. The apparatus of claim 1, wherein the leadscrew extender is shaped to receive motion of the leadscrew along the major axis of the leadscrew.

3. The apparatus of claim 1, wherein the leadscrew extender is shaped to transfer the rotational motion of the leadscrew to the index wheel.

4. The apparatus of claim 1, wherein the plurality of teeth extend radially from a major axis of the index wheel.

5. The apparatus of claim 4, wherein the cantilevered protrusion is positioned to deflect radially from the major axis of the index wheel.

6. The apparatus of claim 1, wherein the dosage meter includes a strain sensor disposed on the cantilevered protrusion to generate the signal indicative of the strain.

7. The apparatus of claim 6, wherein the strain sensor is positioned on a circuit board.

8. The apparatus of claim 1, wherein the dosage meter includes a bracket shaped and positioned to place the cantilevered protrusion in contact with one of the plurality of teeth.

9. The apparatus of claim 8, wherein the bracket includes a columnar portion shaped to receive a portion of the leadscrew and shaped to position the index wheel coaxially with the major axis of the leadscrew.

10. The apparatus of claim 9, wherein the bracket does not receive the rotational motion, and wherein the cantilevered protrusion remains static relative to the rotational motion.

11. The apparatus of claim 1, further comprising:
a housing shaped to accept the cartridge containing the fluid.

12. The apparatus of claim 1, further comprising a controller operatively coupled to the dosage meter and including logic that when executed by the controller causes the apparatus to perform operations including:
tracking the signal output from the dosage meter.

13. The apparatus of claim 12, wherein the controller further includes logic that when executed by the controller causes the apparatus to perform operations including:
registering the signal as an injection event of the dispensed fluid; and
calculating a number of injection events of the fluid.

14. The apparatus of claim 12, wherein the controller further includes logic that when executed by the controller causes the apparatus to perform operations including:
calculating a quantity of the fluid dispensed based on the signal.

15. The apparatus of claim 13, further comprising:
a power source coupled to the controller; and
a transceiver coupled to the controller to send and receive data, wherein the controller further includes logic that when executed by the controller causes the apparatus to perform operations including:
instructing the transceiver to send the data to an external device, wherein the data includes information indicative of the number of injection events.

16. A method of measuring a quantity of fluid dispensed from an apparatus comprising:
rotating an index wheel of the apparatus about a major axis of a leadscrew coaxially received by the index wheel as fluid is dispensed;
inducing a strain in a cantilevered protrusion disposed to engage the index wheel as the index wheel rotates;
generating a signal indicative of the strain in the cantilevered protrusion;
tracking the signal indicative of the strain to determine the quantity of the fluid dispensed; and
registering the signal as an injection event of the fluid and calculating a quantity of the fluid dispensed based on the signal.

17. The method of claim 16, wherein generating the signal indicative of the strain in the cantilevered protrusion includes:
deflecting the cantilevered protrusion with a tooth extending radially from a major axis of the index wheel, wherein the cantilevered protrusion deflects radially from the major axis of the index wheel in response to the tooth pressing against the cantilevered protrusion; and
generating with a strain sensor disposed on the cantilevered protrusion and coupled to a controller the signal.

18. The method of claim 16, wherein tracking the signal indicative of the strain includes storing the signal in memory disposed in the apparatus using a controller coupled to receive the signal.

19. The method of claim 16, further comprising transmitting data, representative of the signal, to a processing device that is distinct from the apparatus, wherein the processing device calculates the quantity of fluid dispensed.

20. An apparatus for measuring an amount of a dispensed fluid, the apparatus comprising:
a dosage meter shaped to couple with a leadscrew and a cartridge containing a fluid for injection, the dosage meter comprising:
an index wheel including a plurality of teeth extending radially from a major axis of the index wheel, wherein the index wheel is shaped to position coaxially with a major axis of the leadscrew and to receive rotational motion from the leadscrew; and a cantilevered protrusion positioned to deflect radially from the major axis of the index wheel due to contact with the plurality of teeth as the index wheel rotates coaxially with the leadscrew inducing a strain in the cantilevered protrusion, wherein the dosage meter outputs a signal indicative of the strain; and a leadscrew extender positioned to be in contact at a first end of the leadscrew extender with a portion of the cartridge and at a second end of the leadscrew extender with an end of the leadscrew.

\* \* \* \* \*